US00PP09510P

United States Patent [19]

Ebihara

[11] Patent Number: Plant 9,510

[45] Date of Patent: Apr. 16, 1996

[54] HYDRANGEA PLANT NAMED 'FRAU MACHIKO'

[75] Inventor: Hiroshi Ebihara, Ninomiya, Japan

[73] Assignee: Miyoshi & Co, Ltd., Tokyo, Japan

[21] Appl. No.: 384,940

[22] Filed: Feb. 7, 1995

[51] Int. Cl.[6] ..... A01H 5/00

[52] U.S. Cl. ..... Plt./67.1

[58] Field of Search ..... Plt./67.1

*Primary Examiner*—James R. Feyrer
*Attorney, Agent, or Firm*—James R. Cypher

[57] ABSTRACT

This invention relates to a new and distinct cultivar of *Hydrangea macrophlla* (Thunb.) named 'Frau Machiko' which originated as a seedling from the inventor's controlled hybridization of the *Hydrangea macrophylla* cultivars 'Madam Blumkock' and 'Silver-Edge' and is distinguished from its parents by the unique pigmentation pattern which gives a cruciform appearance to its florets. Sepal color of 'Frau Machiko' is predominately white with blue or pink pigmentation beginning at the base of the flower and fading to white as it progresses across the length and width of the sepals. Color is deepest in the 5–7 middle veins of the sepals. The sepals of 'Madam Blumkock' are uniformly pigmented one color, while the sepals of 'Silver-Edge' are also uniformly pigmented except the sepal edges are white. The new variety 'Frau Machiko' further possesses the favorable characteristics of a compact growth habit, long lasting large flowers and ability to be easily forced in a greenhouse for flowering in the spring.

1 Drawing Sheet

BACKGROUND OF THE INVENTION

This invention relates to a new and distinct cultivar of the Saxifragaceae family. The botanical name of the plant is *Hydrangea macrophylla* (Thunb.). The varietal denomination is 'Frau Machiko'. The new cultivar originated as a seedling from the inventor's controlled crossing as pollen and seed parents, respectively, the varieties known as 'Madam Blumkock' and 'Silver-Edge' in Tochigi-Prefecture, Japan. 'Frau Machiko' was discovered and selected as one flowering plant within the progeny of the stated parentage in a controlled environment. 'Frau Machiko' is distinguished from its parents and all other varieties of Hydrangea, of which I am aware, by the pigmentation pattern in its sepals which is predominanently white with color radiating out from the apex to give a cruciform appearance to the florets. This new cultivar has been successfully asexually reproduced under controlled environmental conditions at a nursery in Half Moon Bay, Calif. under the direction of the inventor over a three year period with its distinguishing characteristics remaining stable.

'Frau Machiko' is distinguished from its parents and all other varieties of Hydrangea of which I am aware by the pigmentation pattern in its sepals. Sepal color of 'Frau Machiko' is predominately white with blue or pink pigmentation. Sepal pigmentation of individual *Hydrangea macrophylla* plants depends on the nutrients and pH of the growing medium. The pigmentation of 'Frau Machiko' begins at the base of the flower and fades to white as it progresses across the length and width of the sepals. The color is deepest in the 5–7 middle veins of the sepals. The sepal coloration of the pollen parent, 'Madam Blumkock', is uniformly pink. The sepals of seed parent, 'Silver-Edge', have a uniform red pigmentation, with white edges. While there are other Hydrangeas with a coloration pattern on their sepals, none of the other known varieties of Hydrangeas have the particular pattern of 'Frau Machiko' where the sepal is predominately white with color radiating out from the apex to give a cruciform appearance to the florets. The new variety of Hydrangea as described herein is further characterized by its compact growth habit, the ease with which it can be forced in a greenhouse, and its large, long lasting flowers. Mature flowers slowly fade to green and ultimately brown with age.

Asexual reproduction was first accomplished when vegetative cuttings were taken by the inventor from the initially selected plant. Examination of asexually reproduced, successive generations grown in a controlled environment at Half Moon Bay, Calif. show that the combination of characteristics as herein disclosed for 'Frau Machiko' is firmly fixed. Asexual reproduction of successive generations at Half Moon Bay was achieved by taking vegetative cuttings from selected plants, in August of 1991, June of 1992, the spring of 1993 and June of 1994. Each new generation over the three years retained the combination of characteristics as herein disclosed for 'Frau Machiko'.

DESCRIPTION OF THE DRAWINGS

The accompanying drawings consist of color photographs that show the typical plant form, including the inflorescence, foliage, and unique sepal pigmentation pattern. 'Frau Machiko' is shown with a pink and white sepal pigmentation pattern, but a blue and white pigmentation pattern is also possible by manipulation of the nutrient amendments and the pH of the growing medium. The colors are represented as truly as possible using conventional photographic procedures.

DESCRIPTION OF THE NEW PLANT

Figure 1:
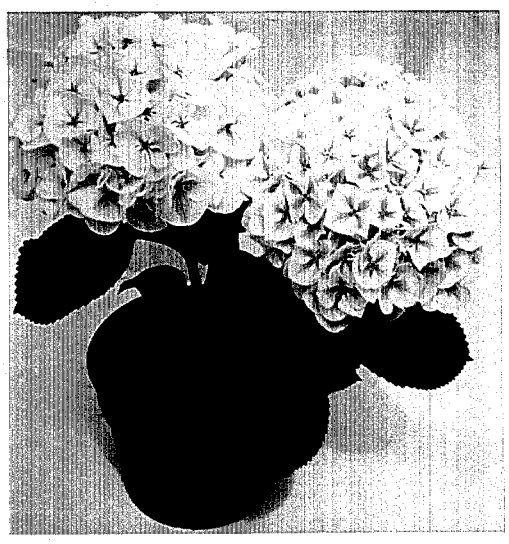
FIG. 1 is a view of the entire plant showing its form, compact growth habit, dark green foliage, inflorescense, and unique sepal pigmentation pattern which gives a cruciform appearance to the florets.
Figure 2:
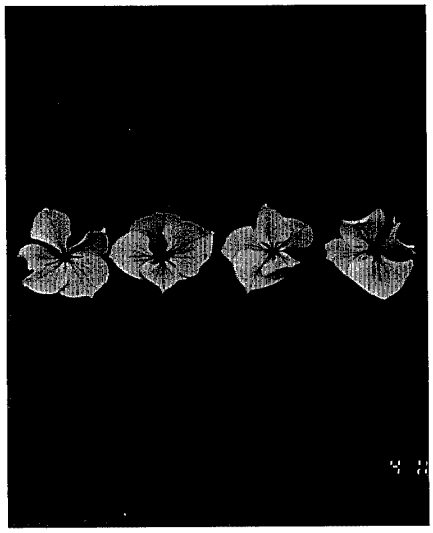
FIG. 2 is a close-up view of the individual florets illustrating the unique color pigmentation pattern of the sepals which gives a cruciform appearance to the florets.
Figure 3:
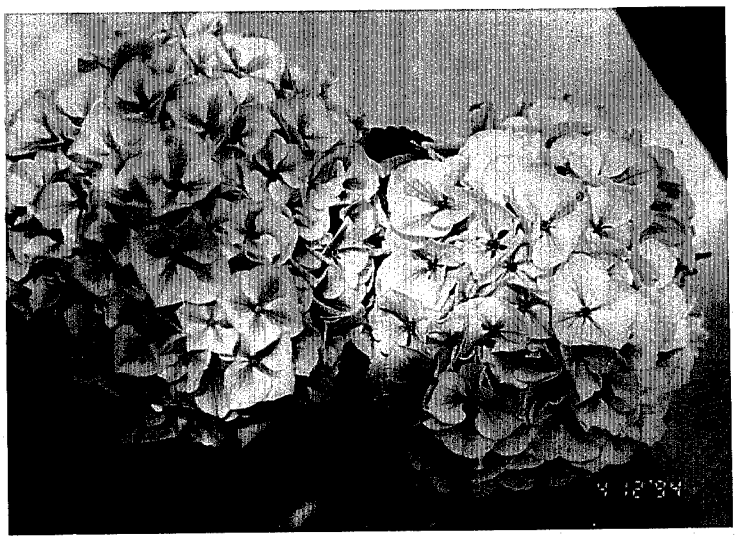
FIG. 3 is a close-up view taken from above the inflorescense of the new cultivar showing its large flower heads and predominanently white sepals with color pigmentation radiating out from the apex giving a cross-like appearance to the florets.

'Frau Machiko' has not been observed under all possible environmental conditions. The phenotype may vary significantly with variations in environment such as temperature, light intensity and day length. The following is a detailed description of the new cultivar as forced under the prevailing daylengths at Half Moon Bay, Calif. under commercial greenhouse conditions at a time appropriate for the sale of the cultivar in the spring. The color determinations were made with The Royal Horticultural Society (R.H.S.) Colour Chart.

THE PLANT

Origin: Seedling.

Parentage:

*Seed parent.*—*Hydrangea macrophylla* DC var. *hortensia* 'Silver-Edge'.

*Pollen parent.*—*Hydrangea macrophylla* DC var. *hortensia* 'Madam Blumkock'.

Classification:

*Botanic.*—*Hydrangea macrophylla* (Thunb.) 'Frau Machiko'.

*Commercial.*—Florist Hydrangea 'Frau Machiko'.

Form: Upright, compact shrub.

Height: Flowering shoots reach 38 cm.

Growth: Upright, vigorous growth habit; forced to bloom in greenhouse without the addition of growth regulators. Flowerhead is large. Flowering shoots often staked to prevent bending of the stem.

Stems: Colorless lenticels lateral buds are green with a reddish tip; reddish coloration above and below leaf attachment sites.

Foliage: Abundant.

*Size of leaf.*—As large as 134 mm long by 92 mm wide.

*Shape of leaf.*—Elliptic with acute base and apex; margins are serrate.

*Texture.*—Glabrous; veins dominate on the underside of the leaf and are sunken on the leaf surface.

*Color.*—Upper side is R.H.S. 137 A (green group); upper side covered by flower is R.H.S. 147 A (Yellow-green group); under side is R.H.S. 137 C (green group); veins are R.H.S. 145 D (yellow-green group).

*Petioles.*—3 cm long.

THE BUD

Form: Globose; with 4 to 5 connate petals. Buds in the very center of the inflorescene are non-sepalous. The majority of buds have sepals.

Size: 3 mm.

Aspect: Smooth.

Rate of opening: Buds with sepals opening more slowly than buds without sepals.

Sepals: Early pigmentation is R.H.S. 145 B to 150 D (yellow-green group).

Arrangement: Borne on 3, 4 or 5 branched panicles.

INFLORESCENCE

Time of blooming: Forced in 70 to 80 days at 15.5° C.

Form: Paniculate. 100 or more individual flowers (florets) per inflorescence. Both sterile, sepalous florets and fertile, non-sepalous florets borne on same panicle.

Size of inflorescence: Individual inflorescence size is dependent on the number of inflorescences. The large inflorescences have been measured with a 25 cm diameter.

Shape: Spherical clusters of numerous small florets; sepalous florets are flat and overlapping one another. Sepals are persistents. Sepals elongate and color as the inflorescence matures. Non-sepalous, fertile florets are inconspicuous and hidden by sepalous florets.

Appearance: Showy.

Persistence: 4 or more weeks.

Fragrance: Faintly sweet.

Fruit: None.

Reproductive organs:

*Stamens.*—7 to 9 stamens. Pollen is white.

*Stigma.*—1 three-pronged stigma.

Sepalous florets:

*Number of sepals.*—4 or 5 sepals per floret, usually 4.

*Aspect of sepals.*—smooth.

*Shape of sepals.*—Reniform with acuminate apex. Edges often wavy.

*Size of sepals.*—Usually 1 dominant sepal, 2 smaller but equally-sized sepals, and 1 small sepal. The largest sepal measured 45 mm wide by 35 mm long.

*Size of one large floret.*—73 mm.

*Coloration of sepals.*—Predominately white with color in sepal radiating out from apex to give a cruciform appearance to the floret, darker at base of sepal, fading to white 1 to 1½ cm from edge. Color generally develops in 5 or 7 of the middle veins. As inflorescences age the coloration of entire sepal fades to cream, then green, and then brown. Sepal color is not detailed using The R.H.S. Colour Chart as the sepal color is determined by the soil pH and nutritional amendments supplied.

I claim:

1. A new and distinct hybrid plant variety of the Saxifragaceae family substantially as herein shown and described.

* * * * *